United States Patent
Elsheikh et al.

(10) Patent No.: US 8,445,736 B2
(45) Date of Patent: May 21, 2013

(54) CATALYTIC GAS PHASE FLUORINATION OF 1230XA TO 1234YF

(75) Inventors: Maher Y. Elsheikh, Wayne, PA (US); Philippe Bonnet, Lyons (FR)

(73) Assignee: Arkema Inc., King of Prussia, PA (US)

( * ) Notice: Subject to any disclaimer, the term of this patent is extended or adjusted under 35 U.S.C. 154(b) by 114 days.

(21) Appl. No.: 12/999,704

(22) PCT Filed: Jun. 23, 2009

(86) PCT No.: PCT/US2009/048214
§ 371 (c)(1),
(2), (4) Date: Jan. 28, 2011

(87) PCT Pub. No.: WO2009/158321
PCT Pub. Date: Dec. 30, 2009

(65) Prior Publication Data
US 2011/0130599 A1    Jun. 2, 2011

Related U.S. Application Data

(60) Provisional application No. 61/075,804, filed on Jun. 26, 2008.

(51) Int. Cl.
*C07C 17/00* (2006.01)

(52) U.S. Cl.
USPC .......................................... 570/165; 570/164

(58) Field of Classification Search
USPC ................................... 570/164, 165
See application file for complete search history.

(56) References Cited

U.S. PATENT DOCUMENTS

| | | | |
|---|---|---|---|
| 5,714,651 | A | 2/1998 | Elsheikh et al. |
| 7,026,520 | B1 | 4/2006 | Mukhopadhyay et al. |
| 7,485,598 | B2 | 2/2009 | Elsheikh et al. |
| 2007/0197842 | A1 | 8/2007 | Mukhopedhyay et al. |
| 2008/0051611 | A1 | 2/2008 | Wang et al. |

FOREIGN PATENT DOCUMENTS

| WO | WO 2007/079432 | 7/2007 |
|---|---|---|
| WO | WO 2008/054781 | 5/2008 |

*Primary Examiner* — Jafar Parsa
(74) *Attorney, Agent, or Firm* — Steven D. Boyd

(57) ABSTRACT

A one reactor, gas phase catalyzed process for the fluorination of 1,1,2,3-tetrachloropropene (1230xa) to produce 1,1,1,2-tetrafluoropropene (1234yf) is disclosed. The process of the present invention is a catalytic, gas phase fluorination using a high pressure activated catalyst which is supported or unsupported. Fluorination products of the formula $CF_3R$, where R is selected from $-CCl=CH_2$, $-CF=CH_2$, $-CF_2-CH_3$, $-CFCl-CH_3$ and mixtures thereof are produced. Co-produced materials are separated from the desired product and recycled to the same reactor.

19 Claims, No Drawings

CATALYTIC GAS PHASE FLUORINATION OF 1230XA TO 1234YF

FIELD OF THE INVENTION

The present invention relates to the gas phase catalyzed fluorination of 1,1,2,3-tetrachloropropene (1230xa) to produce 1,1,1,2-tetrafluoropropene (1234yf). More particularly, the present invention relates to processes wherein 1230xa; optionally containing a low level of polymerization inhibitor, is contacted with hydrogen fluoride (hereafter referred to as "HF") in a gas phase reaction, in the presence of a fluorination catalyst to produce 1234yf. The desired product, 1234yf is known to have utility as a foam blowing agent, refrigerant, aerosol propellant, heat transfer media, fire extinguisher, etc. Furthermore, 1234yf is known to have zero Ozone Depletion Potential (ODP) and very low Global Warming Potential (GWP) of much less than 150.

BACKGROUND OF THE INVENTION

The Montreal Protocol for the protection of the ozone layer mandated the phase out of the use of chlorofluorocarbons (CFCs). Materials more "friendly" to the ozone layer, such as hydrofluorocarbons (HFCs) e.g. HFC-134a replaced chlorofluorocarbons. The latter compounds have proven to be green house gases, causing global warming and were regulated by the Kyoto Protocol on Climate Change. With the continued concern over global climate change there is an increasing need to develop technologies to replace those with high ozone depletion potential (ODP) and high global warming potential (GWP). Though hydrofluorocarbons (HFCs), being non-ozone depleting compounds, have been identified as alternatives to chlorofluorocarbons (CFCs) and hydrochlorofluorocarbons (HCFCs) as solvents, cleaning agents and heat transfer fluids, they still tend to have significant GWP. Hydrofluoroolefins have been identified as potential alternatives with zero ODP and low GWP.

Methods of preparing hydrofluoroalkenes are known. For example, WO2007/079431 discloses processes for the production of fluorinated olefins, including hydrofluoropropenes. The processes which are broadly described as a single reaction or two or more reactions involve fluorination of compound of the formula $C(X)_m CCl(Y)_n C(X)_m$ to at least one compound of formula $CF_3 CF = CHZ$, where each X, Y and Z is independently H, F, Cl, I or Br and each m is independently 1, 2 or 3 and n is 0 or 1.

WO2008/054781 discloses a variety of processes for producing a variety of fluoropropane and halofluoropropenes by reacting halopropanes or halopropenes with HF optionally in the presence of a catalyst.

SUMMARY OF THE INVENTION

The present invention is direct toward a one reactor, gas phase catalyzed process for the fluorination of 1,1,2,3-tetrachloropropene (1230xa) to produce 1,1,1,2-tetrafluoropropene (1234yf). The process of the present invention is a catalytic, gas phase fluorination.

The inventive process employees a high surface area Cr based catalyst which is unsupported or supported (such as on fluorinated alumina, activated carbon, graphite or fluorinated graphite). The catalyst can optionally contain a low level of one or more co-catalyst such as Co, Zn, Mn, and Ni salt. A preferred co-catalyst is nickel. Prior to its use, the catalyst is subjected to activation with HF at high pressure, above about 150 psi, as described in U.S. Pat. No. 7,485,598, incorporated herein by reference. The resulting activated catalyst was discovered to catalytically induce two different chemical processes concurrently: adding HF to an olefin such 1230xa and eliminating HF from a saturated compound such as 1,1,1,2-tetrafluoro-2-chloropropane (244bb), 1,1,1,2,2-pentafluoropropane (245cb) and/ or 1,1,1,2,3-pentafluoropropane (245eb). The level of the conversion and selectivity of the desired product can vary according to the processing conditions. One feature of the present invention is the preferred use of a single catalyst in a single reactor which can dehydrofluorinate co-products such as 245cb and/or 245eb in a recycle stream into the desired product, 1234yf, In addition, other co-produced underfluorinated intermediates such as 1233xf and 244bb which are produced as part of the fluorination reaction can also be recycled to the reactor. The process of the present invention can be run continuously. Catalyst deterioration or deactivation is minimized by using a low level of oxygen fed to the reactor as air or other oxygen containing gas. The feedstock is chloroolefins. Chloroolefins are vulnerable to polymerization which can cause catalyst deactivation. The co-feeding of a low level of a polymerization inhibitor, such as p-methoxyphenol, can control such polymerization and extend the life of the catalyst as described in U.S. Pat. No. 5,714,651, incorporated herein by reference. The presence of low level of a polymerization inhibitor such as p-methoxyphenol can inhibit the polymerization of chloroolefins such as 1,1-dichloroethylene. The process of the present invention is directed towards the preparation of fluorination products of the formula $CF_3R$, where R is selected from $-CCl=CH_2$, $-CF=CH_2$, $-CF_2-CH_3$, $-CFCl-CH_3$, $-CHF-CH_2F$ and mixtures thereof The process of the present invention can be summarized with the following schematic.

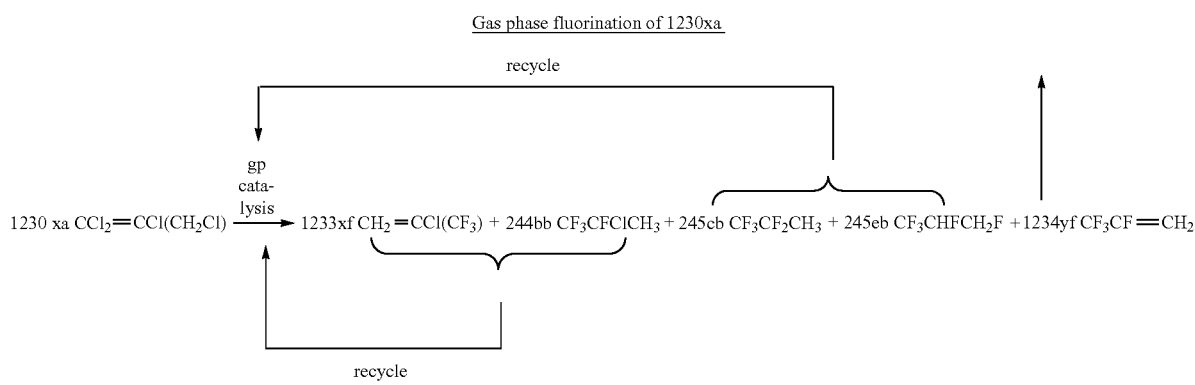

Gas phase fluorination of 1230xa

The process comprises contacting 1230xa, optionally with a polymerization inhibitor, with HF in the gas phase in the presence of a chromium based catalyst, supported or unsupported, to obtain the desired product 1234yf. The chromium based catalyst, supported or unsupported, of the present invention is activated by contact with HF at high pressure, that is pressure above about 150 psi. The chromium based catalyst may optionally include one or more co-catalysts selected from cobalt, nickel, zinc, and manganese. An oxygen containing oxidizing agent is fed to the reactor to maintain catalyst activity. The oxygen can be fed as a pure gas or as an oxygen containing gas such as air. A polymerization inhibitor may also be fed to the reactor to maintain catalyst activity. Co-products produced by the fluorination reaction such as F245cb ($CF_3$—$CF_2$—$CH_3$), F1233xf ($CF_3$—$CCl$=$CH_2$), F244bb ($CF_3$—$CFCl$—$CH_3$), 245eb ($CF_3$ CHF $CH_2$F) and unreacted material such as HF and F1230xa can be recycled to the same reactor. The process can be carried out via a continuous or batch process. The desired product 1234yf is known to have utility as a foam blowing agent, refrigerant, aerosol propellant, heat transfer media, fire extinguisher etc. Furthermore, the 1234yf product is known to have a zero Ozone Depletion Potential (ODP) and very low Global Warming Potential (GWP) of much less than 150, low flammability and non toxic

DETAILED DESCRIPTION OF THE INVENTION

The process of the present invention comprises the gas phase, catalyzed fluorination of 1230xa. The catalyst is preferably a chromium based catalyst which can optionally contain low levels of one or more co-catalysts selected from cobalt, nickel, zinc or manganese, prepared by a processes know in the art, such as impregnation, mixed powder and the like. The catalyst can be supported or unsupported. For supported catalyst, the catalyst support can be selected from materials known in the art to be compatible with HF at higher temperature and pressure. For example, fluorinated alumina, prefluorinated activated carbon, graphite or fluorinated graphite are suitable catalyst supports. A preferred catalyst is a high surface area unsupported chromium oxide catalyst. The catalyst is activated before use. The catalyst activation comprises a high pressure, above 150 psi, procedure wherein the catalyst bed is heated to about 370-380° C., preferably with a continuous flow of nitrogen, after which a mixture of approximately equal volumes of HF and air or nitrogen (preferably nitrogen) are fed over the catalyst bed. The catalyst activation process is as described in U.S. Pat. No. 7,485,598, incorporated herein by reference. Other fluorinated organic compounds such as $CHF_2Cl$, $CHF_3$, $CF_3CH_2F$, CF3CH2Cl and the like can be used for activation. Typically the high pressure catalyst activation procedure takes about 18 hours.

The resulted high-pressure activated catalyst has a high surface area, such as from about 20 to about 250 square meters per gram. The fluorine content varies between about 20 to 25 weight %. The pore volume has an average value between 0.1 to 0.4 m³/g. Crushing strength is between about 20 to 30 lb/gm. Percent attrition is on average between 1 to 5 weight % and $Cr^{(VI)}$ level must be between in the range of 100 to 300 ppm. The level of the co-catalyst, when present, can be varied between 1 to 10 weight %, preferable between 1 to 5 weight %. Co-catalyst can be added to the catalyst by processes known in the art such as adsorption from an aqueous or organic solution, followed by solvent evaporation. A preferred catalyst is pure chromium oxide with nickel as a co-catalyst. Alternatively the co-catalyst can be physically mixed with the catalyst via grinding to produce an intimate mixture. An alternative catalyst is a mixed chromium/nickel catalyst supported on fluorinated alumina. U.S. Pat. No. 5,731,481, incorporated herein by reference, discloses a method of preparation of this alternative catalyst which would be activated as described hereinabove.

Chromium based catalysts, activated via the high pressure process described above, have been found to be useful for fluorinating 1230xa in a catalyzed, gas phase fluorination process to produce the desired product, 1234yf, with high conversion of the 1230xa. The 1230xa fluorination process involves contacting 1230xa, preferably inhibited with a polymerization inhibitor, with HF in the reaction zone in a gas phase, under conditions sufficient to convert the 1230xa to fluorination products such as $CF_3R$, where R is selected from —$CCl$=$CH_2$, —$CF$=$CH_2$, —$CF_2$—$CH_3$, —$CFCl$—$CH_3$, —$CHF$—$CH_2F$ and mixtures thereof, HF and HCl. The HF:1230xa molar ratio is typically from about 2:1 to 50:1, but is preferably from about 5:1 to about 30:1. Temperatures of the catalyst bed can vary from about 30° C. to about 410° C. and are preferably from about 100° C. to about 350° C. Pressures are typically from about atmospheric to about 400 psig, preferably from 20 about 300 psig. An oxygen co-feed is used to extend the catalyst lifetime, typically in an amount of from about 0.005 to about 3 mole % of oxygen per 1230xa. The oxygen can be introduced as an oxygen-containing gas such as air, pure oxygen, or an oxygen/nitrogen mixture. A polymerization inhibitor can be used to extend the catalyst life, typically in a concentration of from abut 50-1000 ppm, more preferably between 100-500 ppm. The polymerization inhibitor can be p-methoxyphenol, t-amylphenol, limonene, d,1-limonene, quinones, hydroquinones, epoxides, amines and mixtures thereof. The preferred polymerization inhibitor is p-methoxyphenol or t-amylphenol.

Contact times (catalyst volume divided by the total flow rate of reactants and co-feeds, adjusted to the operating pressure and temperature) are preferably from about 1 to about 500 seconds, more preferably from about 1 to about 180 seconds.

The desired product, 1234yf, can be separated from the other co-produced products present in the reaction mixture by as variety of means known in the art such as distillation (including extractive distillation) or adsorption. A preferred method of separating the preferred product comprises stripping HCl from the reaction mixture exiting the reactor in a distillation column. Then, in a second distillation zone, the lower boiling product 1234yf can be separated from unreacted products such HF and F1230xa, intermediates such F1233xf and 244bb and co-products such as F245cb and 245eb, all the latter being recycled to the reactor in a preferred single reactor process, as an alternative, multi-step processes can be employed. This second distillation zone can use one-step distillation or multi steps. As used herein, percentage are by weight percent unless specified otherwise.

EXAMPLE 1

High Pressure Activation of $Cr_2O_3$ Catalyst

A $Cr_2O_3$ catalyst was activated at 235 psig and 350° C. using HF and nitrogen gas. The chemical and physical properties of the resulting catalyst are shown in Table 1.

TABLE 1

Summary of the physical and chemical properties of high pressure activated catalyst

| | |
|---|---|
| % F Content | 22.2% (weight) |
| Surface Area m$^2$/g[1] | 43.9 |
| Pore Volume m$^3$/g[2] | 0.19 |
| Crush Strength lb[3] | 23.30 |
| Cr$^{+6}$ level | 201.00 ppm |
| % Attrition[4] | 3.9 |

[1] Surface area was determined by the BET surface area by Micrometrics ASAP 2400
[2] Pore volume was evaluated using xylene porosity measurement.
[3] Crush strength was evaluated by applying a specified rate of compression, until the intergrity of the catalyst is compromised.
[4] Percent Attrition was evaluated by using ASTM D-4058-92 Standard test method for attrition

EXAMPLES 2-3

Fluorination of 1230xa Using Catalyst Activated at High Pressure, in the Presence of Polymerization Inhibitor A catalyst, obtained from Example 1 (52.4 grams; density 1.22 g/cc) could be placed in a 1"×12", vertical fixed bed reactor made out of Hastelloy C. The reactor would be heated using a three-zone electric tube furnace. The reactor inlet fittings would include inlets for HF gas, organic feed (1230xa), and air. Liquid HF feed would be measured and controlled using a liquid mass flow meter controller. The liquid HF would be vaporized using a pre-heater prior to feeding to the reactor. The organic (1230xa, containing p-methoxyphenol 200 ppm) would be fed using a high pressure ISCO pump. Air feed would be controlled and measured using gas mass flow meter controllers. The HF to 1230xa molar ratio could be varied from 20/1 to 30/1 in the presence of oxygen (3% by volume). The reactants would be fed to the reactor at 330° C. Pressure would be adjusted to 150 prig, using down stream pressure regulator. The reaction products would be continuously removed from the reactor. After scrubbing the acid using a 15% KOH solution and drying the organic products, using an anhydrous CaSO$_4$ bed, the dry organic product would be analyzed, using GC. Table 2 summarizes the expected results of gas chromatographic analysis of the products. Increasing the molar ratio from 20/1 to 30/1 would be expected to show an increase in the level of 1234yf and 245cb produced, with a decrease in 1233xf produced. Table 2 summarizes the expected results.

TABLE 2

One step gas phase fluorination of 1230xa to 1234yf Catalyst, high pressure activated Cr$_2$O$_3$, oxygen 0.5 volume %, p-methoxyphenol 200 ppm

| | Example | |
|---|---|---|
| | 2 | 3 |
| Temperature (° C.) | 330 | 330 |
| Pressure (psi) | 150 | 150 |
| Contact Time (sec) | 28 | 19 |
| Molar Ratio (HF/1230xa) | 20/1 | 30/1 |
| O$_2$ Feed (% weight) | .5 | .5 |
| % Conversion | 100 | 100 |
| 1234yf | 11.5 | 15.5 |
| 245cb | 20.7 | 31.2 |
| 1233xf | 66.6 | 51.5 |
| 244bb | 0.7 | 0.5 |
| 245eb | 0.1 | 0.4 |
| others | 0.4 | 0.9 |

1234yf is CF$_3$CF=CH$_2$;
245cb is CF$_3$CF$_2$CH$_3$;
1233xf is CF$_3$CCl=CH$_2$;
244bb is CF$_3$CFClCH$_3$;
245eb is CF$_3$CHF CH$_2$F

EXAMPLE 4

Fluorination of 1230xa in Absence of Oxygen Co-feed and in the Presence of a Polymerization Inhibitor The process described in Example 2 could be carried out in the absence of oxygen co-feed and in the presence of polymerization inhibitor, 200 ppm of p-methoxyphenol. Conversion would be expected to decrease from a high of about 99% to below 50% after running continuously for 100 hours due to catalyst deactivation. The product and co-distribution would be expected to be similar to the selectivity described in Table 2.

EXAMPLE 5

Fluorination of 1230xa, in Absence of the Polymerization Inhibitor, and in the Presence of Oxygen Co-feed Fluorination of 1230xa could be repeated as in Example 4. No polymerization inhibitor would be added and the oxygen co-feed would be 0.5 volume %. In this case the conversion would be expected to decrease from about 99% to below 50% within approximately 18 hours. The level of co-products identified as fluorinated ketones would be expected to increase to approximately 0.5%.

EXAMPLE 6-7

Fluorination of 1230xa with 1233xf 244bb, 245cb and 245eb

The process described in Examples 2 and 3 could be repeated with a feed of 1230xa 76% wt., in combination with underfluorinated materials 1233xf 8% wt., 244bb 6% wt., 245cb 4% wt. and 245eb 6% wt. using the catalyst and processing conditions, described in Example 2 and 3. Table 3 summarizes the expected results

TABLE 3

| | Example | |
|---|---|---|
| | 6 | 7 |
| T C | 330 | 330 |
| P PSI | 150 | 150 |
| CT sec | 28 | 19 |
| MR HF/organic | 20/1 | 30/1 |
| O$_2$ % | 3% | 3% |

TABLE 3-continued

| | Example | |
|---|---|---|
| | 6 | 7 |
| % Conversion | 100 | 100 |
| 1234yf | 18.5 | 20.5 |
| 245cb | 8.5 | 11.5 |
| 1233xf | 56 | 52 |
| 244bb | 15.5 | 13.5 |
| 245eb | 1 | 1.6 |
| others | .5 | .8 |

While the present invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A process for preparing 1,1,1,2-tetrafluoropropene, comprising
contacting, 1,1,2,3-tetrachloropropene with hydrogen fluoride in gas phase in the presence of a chromium fluorination catalyst, and an oxygen containing oxidizing agent, under conditions sufficient to directly produce, in a single reaction step, a reaction mixture comprising 1,1,1,2-tetrafluoropropene and at least one compound of formula $CF_3R$, where R is selected from $—CCl=CH_2$, $—CF_2—CH_3$, $—CFClCH_3$ and $CHF—CH_2F$;
removing HCl from said reaction mixture;
separating 1,1,1,2-tetrafluoropropene from said reaction mixture; and
recycling to the reactor hydrogen fluoride, at least one compound of formula $CF_3R$, where R is selected from $—CCl=CH_2$, $—CF_2—CH_3$, $—CFClCH_3$ and $—CHF CH_2F$
wherein said fluorination catalyst is activated with hydrogen fluoride at a pressure above about 150 psi.

2. The process as in claim 1 wherein said chromium fluorination catalyst is supported or unsupported.

3. The process of claim 2 wherein said chromium fluorination catalyst is supported on a support selected from fluorinated alumina, fluorinated chromia, fluorinated activated carbon or graphite carbon.

4. The process of claim 1 wherein said chromium fluorination catalyst further comprises a co-catalyst selected from Ni, Co, Zn, Mn or mixtures thereof.

5. The process of claim 1 wherein said 1,1,2,3-tetrachloropropene includes a polymerization inhibitor.

6. The process of claim 5 wherein said polymerization inhibitor is selected from the group consisting of p-methoxyphenol, t-amylphenol, limonene, d,1-limonene, quinones, hydroquinones, epoxides, amines and mixtures thereof.

7. The process of claim 4 wherein said co-catalyst is present in an amount from about 1-10 weight % of said fluorination catalyst.

8. The process of claim 1 wherein said chromium fluorination catalyst comprises supported chromium catalyst with nickel co-catalyst.

9. The process of claim 1 wherein said oxidizing agent is selected from air or oxygen.

10. The process of claim 9 wherein said oxidizing agent is added in an amount of from about 0.005 to about 3 mole % of oxygen relative to 1230xa.

11. The process of claim 9 wherein said oxidizing agent is added in an amount of from about 0.05 to about 1 mole % of oxygen relative to 1230xa.

12. The process of claim 1 wherein said separating is via one or more distillation operations.

13. The process of claim 1 wherein the molar ratio of HF to 1230xa is from about 2:1 to about 50:1.

14. The process of claim 1 wherein the molar ratio of HF to 1230xa is from about 5:1 to about 30:1.

15. The process of claim 1 wherein the temperature of the catalyst ranges from about 30° C. to about 410° C.

16. The process of claim 1 wherein the temperature of the catalyst ranges from about 100° C. to about 350° C.

17. The process of claim 1 wherein the pressure ranges from about atmospheric to about 400 psig.

18. The process of claim 1 wherein the pressure ranges from about 20 psig to about 300 psig.

19. The process of claim 1 wherein said contacting is a continuous operation.

* * * * *